(12) United States Patent
Gross

(10) Patent No.: US 8,196,580 B2
(45) Date of Patent: Jun. 12, 2012

(54) IMPLANTABLE RESPIRATION THERAPY DEVICE

(76) Inventor: Yossi Gross, Moshav Mazor (IL)

( * ) Notice: Subject to any disclaimer, the term of this patent is extended or adjusted under 35 U.S.C. 154(b) by 755 days.

(21) Appl. No.: 12/300,363

(22) PCT Filed: May 10, 2007

(86) PCT No.: PCT/IL2007/000572
§ 371 (c)(1),
(2), (4) Date: Dec. 18, 2008

(87) PCT Pub. No.: WO2007/132449
PCT Pub. Date: Nov. 22, 2007

(65) Prior Publication Data
US 2009/0107511 A1    Apr. 30, 2009

Related U.S. Application Data

(60) Provisional application No. 60/799,951, filed on May 11, 2006.

(51) Int. Cl.
*A61F 2/04*     (2006.01)
*A61F 2/20*     (2006.01)
*A61M 16/00*    (2006.01)
*A62B 7/00*     (2006.01)
*A62B 9/06*     (2006.01)

(52) U.S. Cl. .................. 128/204.18; 128/207.14; 623/9; 623/23.64

(58) Field of Classification Search .............. 128/204.18, 128/206.29, 207.14–207.17, 200.24, 200.26, 128/203.12, 203.14, 204.21–204.23, 205.18; 623/9, 23.64–23.65; *A61F 2/04; A61M 16/00; A62B 7/00, 9/06*
See application file for complete search history.

(56) References Cited

U.S. PATENT DOCUMENTS

| | | | |
|---|---|---|---|
| 3,470,876 A | 10/1969 | Barchilon | |
| 3,826,265 A | 7/1974 | Giori et al. | |
| 4,017,858 A | 4/1977 | Kuipers | |
| 4,313,431 A | 2/1982 | Frank et al. | |
| 4,524,466 A * | 6/1985 | Hall et al. | 623/3.25 |
| 4,527,549 A | 7/1985 | Gabbay | |
| 4,583,523 A | 4/1986 | Kleinke et al. | |
| 4,615,332 A | 10/1986 | Buess et al. | |
| 4,753,221 A | 6/1988 | Kensey et al. | |
| 4,809,676 A | 3/1989 | Freeman | |
| 4,849,692 A | 7/1989 | Blood | |
| 4,919,647 A | 4/1990 | Nash | |
| 4,938,766 A | 7/1990 | Jarvik | |
| 5,123,922 A | 6/1992 | Berg | |
| 5,156,154 A | 10/1992 | Valenta, Jr. et al. | |
| 5,324,177 A | 6/1994 | Golding et al. | |
| 5,325,845 A | 7/1994 | Adair | |

(Continued)

OTHER PUBLICATIONS

Stock et al., "Development and application of a real-time monitoring and feedback system for deep inspiration breath hold based on external marker tracking", Med. Phys. Aug. 2006; 33(8): 2868-77—an abstract.

(Continued)

*Primary Examiner* — Oren Ginsberg
(74) *Attorney, Agent, or Firm* — Fish & Richardson P.C.

(57) ABSTRACT

Apparatus (10) is provided, including a housing (26) configured to be implanted in a trachea (20) of a patient and a propeller (22), coupled to the housing. The propeller is configured to generate a positive pressure in the trachea while the propeller is in the trachea. Other embodiments are also described.

42 Claims, 3 Drawing Sheets

U.S. PATENT DOCUMENTS

| | | | |
|---|---|---|---|
| 5,372,587 A | 12/1994 | Hammerslag et al. | |
| 5,553,611 A | 9/1996 | Budd et al. | |
| 5,558,091 A | 9/1996 | Acker et al. | |
| 5,611,335 A | 3/1997 | Makhoul et al. | |
| 5,697,377 A | 12/1997 | Wittkampf et al. | |
| 5,744,953 A | 4/1998 | Hansen | |
| 5,749,855 A | 5/1998 | Reitan | |
| 5,928,132 A | 7/1999 | Leschinsky | |
| 5,972,026 A | 10/1999 | Laufer et al. | |
| 6,030,336 A | 2/2000 | Franchi et al. | |
| 6,063,085 A | 5/2000 | Tay et al. | |
| 6,083,260 A | 7/2000 | Aboul-Hosn | |
| 6,165,164 A | 12/2000 | Hill et al. | |
| 6,168,624 B1 | 1/2001 | Sudai et al. | |
| 6,233,476 B1 | 5/2001 | Strommer et al. | |
| 6,245,007 B1 | 6/2001 | Bedingham et al. | |
| 6,258,100 B1 | 7/2001 | Alferness et al. | |
| 6,283,988 B1 | 9/2001 | Laufer et al. | |
| 6,293,951 B1 | 9/2001 | Alferness et al. | |
| 6,299,575 B1 | 10/2001 | Bolling | |
| 6,387,037 B1 | 5/2002 | Bolling et al. | |
| 6,445,943 B1 | 9/2002 | Ferre et al. | |
| 6,450,942 B1 | 9/2002 | Lapanashvili et al. | |
| 6,490,474 B1 | 12/2002 | Willis et al. | |
| 6,572,652 B2 | 6/2003 | Shaknovich | |
| 6,593,884 B1 | 7/2003 | Gilboa et al. | |
| 6,636,757 B1 | 10/2003 | Jascob et al. | |
| 6,662,804 B2 | 12/2003 | Ortiz | |
| 6,679,264 B1 | 1/2004 | Deem et al. | |
| 6,690,963 B2 | 2/2004 | Ben-Haim et al. | |
| 6,694,979 B2 | 2/2004 | Deem et al. | |
| 6,730,118 B2 | 5/2004 | Spenser et al. | |
| 6,757,563 B2 | 6/2004 | Sweeney | |
| 6,783,536 B2 | 8/2004 | Vilsmeier et al. | |
| 6,784,660 B2 | 8/2004 | Ashe | |
| 6,836,745 B2 | 12/2004 | Seiler et al. | |
| 6,947,788 B2 | 9/2005 | Gilboa et al. | |
| 6,990,427 B2 | 1/2006 | Kirsch et al. | |
| 6,994,094 B2 | 2/2006 | Schwartz et al. | |
| 7,025,784 B1 | 4/2006 | Blom et al. | |
| 7,115,127 B2 | 10/2006 | Lindenbaum et al. | |
| 7,130,700 B2 | 10/2006 | Gardeski et al. | |
| 7,189,240 B1 | 3/2007 | Dekel | |
| 7,472,702 B2 * | 1/2009 | Beck et al. | 128/204.23 |
| 7,985,254 B2 * | 7/2011 | Tolkowsky | 623/9 |
| 2002/0103413 A1 | 8/2002 | Bugge et al. | |
| 2002/0124848 A1 * | 9/2002 | Sullivan et al. | 128/204.21 |
| 2003/0127090 A1 | 7/2003 | Gifford et al. | |
| 2003/0135086 A1 | 7/2003 | Khaw et al. | |
| 2003/0229319 A1 * | 12/2003 | Mitchnick | 604/265 |
| 2004/0097783 A1 | 5/2004 | Peters et al. | |
| 2004/0106880 A1 | 6/2004 | Weng et al. | |
| 2004/0116769 A1 | 6/2004 | Jassawalla et al. | |
| 2004/0158294 A1 | 8/2004 | Thompson | |
| 2004/0237966 A1 | 12/2004 | Tanaka | |
| 2005/0015866 A1 | 1/2005 | Steinert | |
| 2005/0025816 A1 | 2/2005 | Tanaka | |
| 2005/0103340 A1 | 5/2005 | Wondka | |
| 2005/0159640 A1 | 7/2005 | Barbut et al. | |
| 2005/0171508 A1 | 8/2005 | Gilboa | |
| 2006/0027234 A1 * | 2/2006 | Gradon et al. | 128/204.21 |
| 2006/0122456 A1 | 6/2006 | LaRose et al. | |
| 2006/0161233 A1 | 7/2006 | Barry et al. | |
| 2006/0178552 A1 | 8/2006 | Gross | |
| 2006/0195004 A1 | 8/2006 | Jarvik | |
| 2006/0276775 A1 | 12/2006 | Rosenberg et al. | |
| 2008/0125760 A1 | 5/2008 | Gilboa | |

OTHER PUBLICATIONS

Wilmot C. Ball Jr., "Interactive respiratory physiology", MD, Johns Hopkins School of Medicine, Office of Medical Informatics Education, 1996.

Tsuda et al., "Chaotic mixing deep in the lung", Proceedings of the National Academy of Sciences of the USA, Jul. 2002.

Brightling, "Sputum induction in asthma", Chest 2006.

Domenico Spina, "Drugs for the treatment of respiratory diseases", Cambridge University Press, 2003.

Clauses, et al., "Assisted Circulation: 1. The arterial Counterpulsator", Journal of Thoracic and Cardiovascular Surgery, 41:447, Apr. 1961.

G. Gregoratos, et al., "ACC/AHA/NASPE 2002 Practice Guidelines", JACC vol. 40, No. 9, 2002, Nov. 6, 2002, 1703-19.

F. Unger, et al., "The Windkesselventricle with guiding balloon as a new approach for assisted circulation", Medical Instrumentation, vol. 10, No. 5, Sep.-Oct. 1976.

W.C. Birtwell, et al., "The evolution of counterpulsation techniques", Medical Instrumentation, vol. 10, No. 5, Sep.-Oct. 1976.

* cited by examiner

IMPLANTABLE RESPIRATION THERAPY DEVICE

CROSS-REFERENCES TO RELATED APPLICATIONS

The present application is the U.S. national phase application under 35 U.S.C. §371 of International Patent Application No. PCT/IL07/000572, filed May 10, 2007, which claims the benefit of US Provisional Application 60/799,951, filed May 11, 2006, entitled, "Implantable respiration therapy device," which is incorporated herein by reference. The International Application published in English on Nov. 22, 2007 as WO 2007/132449 under PCT Article 21(2).

FIELD OF THE INVENTION

The present invention relates generally to implantable medical devices, and specifically to implantable medical devices for providing respiration therapy.

BACKGROUND OF THE INVENTION

Mechanical ventilation assists or replaces spontaneous breathing. Positive pressure ventilation is the provision of air under pressure into the lungs, either invasively or non-invasively. Invasive positive-pressure ventilation is the delivery of positive pressure via an invasive artificial airway, such as an endotracheal tube or tracheostomy tube, while noninvasive positive-pressure ventilation (NPPV) is the delivery of positive pressure without such an invasive artificial airway, instead using a nasal or face mask.

Ventilation modes include volume ventilation, pressure-controlled ventilation, bi-level positive airway pressure (BIPAP) ventilation, inspiratory positive airway pressure (IPAP) ventilation, continuous positive airway pressure (CPAP) ventilation, and pressure-controlled ventilation (PCV). CPAP ventilation delivers a constant pressure, which assists inspiration and resists expiration. BIPAP ventilation delivers a higher pressure during inspiration, and a lower pressure during expiration.

SUMMARY OF THE INVENTION

In some embodiments of the present invention, apparatus for providing invasive positive-pressure ventilation comprises a tracheal implant comprising a propeller. One or more blades of the propeller rotate to deliver positive pressure to the trachea. The implant can be used with or without supplemental oxygen.

For some applications, the implant is used to treat a patient suffering from emphysema. The implant delivers a low level of positive pressure that provides a constant state of expansion of alveoli. Patients suffering from emphysema generally must first inhale in order to expand the alveoli, which are able to effectively exchange oxygen only upon expansion. The constant state of expansion provided by the implant enables the alveoli to exchange oxygen during a greater portion of inhalation than is achievable in the absence of the applied constant state of expansion. In addition, such constant expansion typically reduces friction/shear injury to alveoli associated with the continuous inflation and deflation of the alveoli. Alternatively, the implant is used to treat other conditions, such as congestive heart failure, a pulmonary condition (e.g., pulmonary edema or chronic obstructive pulmonary disease (COPD)), or sleep apnea (e.g., obstructive sleep apnea).

There is therefore provided, in accordance with an embodiment of the present invention, apparatus including:

a housing configured to be implanted in a trachea of a patient; and a propeller, coupled to the housing, and configured to generate a positive pressure in the trachea while the propeller is in the trachea.

In an embodiment, the apparatus includes circuitry configured to:

drive the propeller to generate the positive pressure, and regulate the positive pressure generated by the propeller by setting a rate of rotation of the propeller.

In an embodiment, the propeller includes one or more blades, and the apparatus includes circuitry configured to:

drive the propeller to generate the positive pressure, and regulate the positive pressure generated by the propeller by setting an angle of inclination of the blades.

In an embodiment, the propeller includes one or more blades, and the apparatus includes a tube that surrounds at least one element of the apparatus selected from the group consisting of: the housing, and the blades.

In an embodiment, the propeller includes one or more blades, the housing is, shaped so as to define an inlet and outlet that together define a flow path, and the blades are positioned within the housing in the flow path.

In an embodiment, the apparatus is configured to treat a condition of the patient selected from the group consisting of: congestive heart failure, a pulmonary condition, pulmonary edema, chronic obstructive pulmonary disease (COPD), sleep apnea, obstructive sleep apnea, and emphysema.

In an embodiment, the apparatus includes circuitry configured to drive the propeller to generate the positive pressure in accordance with a schedule.

In an embodiment, the apparatus includes circuitry configured to:

drive the propeller to generate the positive pressure, and drive the propeller to reduce a level of operation when the patient is sleeping.

In an embodiment, the housing includes an anchoring mechanism, which is configured to couple the housing to an inner surface of the trachea.

In an embodiment, the housing is releasably coupled to the anchoring mechanism.

In an embodiment, the anchoring mechanism includes a stent, which is sized to adhere to the inner surface of the trachea.

In an embodiment, the anchoring mechanism includes a plurality of wire springs, which are configured, upon expansion, to come in contact with the inner surface of the trachea.

In an embodiment, the springs are generally spiral-shaped.

In an embodiment, the propeller is configured to generate the positive pressure at a low level that provides a constant state of expansion of alveoli of the patient.

In an embodiment, the apparatus is configured to treat emphysema of the patient.

In an embodiment, the apparatus includes circuitry configured to drive the propeller to generate the positive pressure in a ventilation mode.

In an embodiment, the ventilation mode is selected from the group consisting of: volume ventilation, pressure-controlled ventilation, bi-level positive airway pressure (BIPAP) ventilation, inspiratory positive airway pressure (IPAP) ventilation, continuous positive airway pressure (CPAP) ventilation, and pressure-controlled ventilation (PCV), and the circuitry is configured to drive the propeller to generate the positive pressure in the selected ventilation mode.

In an embodiment, the circuitry is configured to drive the propeller to generate a controllable level of positive end expiratory pressure (PEEP).

In an embodiment, the apparatus includes a sensor configured to sense at least one parameter of respiration of the patient, the circuitry is configured to drive the propeller responsively to the at least one parameter.

In an embodiment, the sensor includes a pressure sensor.

In an embodiment, the pressure sensor is configured to detect pressure fluctuations between 0.05 and 1 Hz.

In an embodiment, the circuitry is configured to detect pressure fluctuations between 0.05 and 1 Hz.

In an embodiment, the apparatus includes:
an activity sensor; and
circuitry, which is configured to modulate a parameter of operation of the propeller responsively to a sensed level of activity of the patient.

In an embodiment, the activity sensor is selected from the group consisting of: an accelerometer, a respiration rate monitor, and a heart rate monitor.

In an embodiment, the circuitry is configured to increase a speed of the propeller in response to an increase in the sensed level of activity.

In an embodiment, for administering a drug, the housing is shaped so as to define a drug reservoir configured to hold the drug, and the apparatus includes an application mechanism, coupled to the housing, and configured to release the drug from the reservoir into the trachea.

In an embodiment, the application mechanism is configured to spray the drug into the trachea.

In an embodiment, the apparatus includes circuitry configured to:
actuate the application mechanism, and
regulate at least one parameter of administration of the drug selected from the group consisting of: a dosage of the administration, and a timing of the administration.

In an embodiment, the circuitry is configured to receive a signal, and to regulate the administration of the drug responsively to the signal.

In an embodiment, the signal is selected from the group consisting of: an acoustic signal indicative of an onset of a transient pathological respiratory condition, and a pressure signal indicative of an onset of a transient pathological respiratory condition, and the circuitry is configured to receive the selected signal, and to regulate the administration responsively thereto.

There is further provided, in accordance with an embodiment of the present invention, apparatus for administering a drug, the apparatus including:
a housing configured to be implanted in a trachea of a patient, the housing shaped so as to define a drug reservoir configured to hold the drug; and
an application mechanism, coupled to the housing, and configured to release the drug from the, reservoir into the trachea.

In an embodiment, the application mechanism is configured to spray the drug into the trachea.

In an embodiment, the apparatus includes circuitry configured to:
actuate the application mechanism, and
regulate at least one parameter of administration of the drug selected from the group consisting of: a dosage of the administration, and a timing of the administration.

In an embodiment, the circuitry is configured to receive a signal, and to regulate the administration of the drug responsively to the signal.

In an embodiment, the signal is selected from the group consisting of: an acoustic signal indicative of an onset of a transient pathological respiratory condition, and a pressure signal indicative of an onset of a transient pathological respiratory condition, and the circuitry is configured to receive the selected signal, and to regulate the administration responsively thereto.

There is still further provided, in accordance with an embodiment of the present invention, a method including:
implanting a propeller in a trachea of a patient; and
rotating the propeller to generate a positive pressure in the trachea.

In an embodiment, the method includes providing supplemental oxygen in conjunction with rotating the propeller.

There is yet further provided, in accordance with an embodiment of the present invention, a method for administering a drug, the method including:
implanting, in a trachea of a patient, a drug reservoir configured to hold the drug; and
releasing the drug from the reservoir into the trachea.

The present invention will be more fully understood from the following detailed description of embodiments thereof, taken together with the drawings, in which:

DETAILED DESCRIPTION OF EMBODIMENTS

Figure 1A:
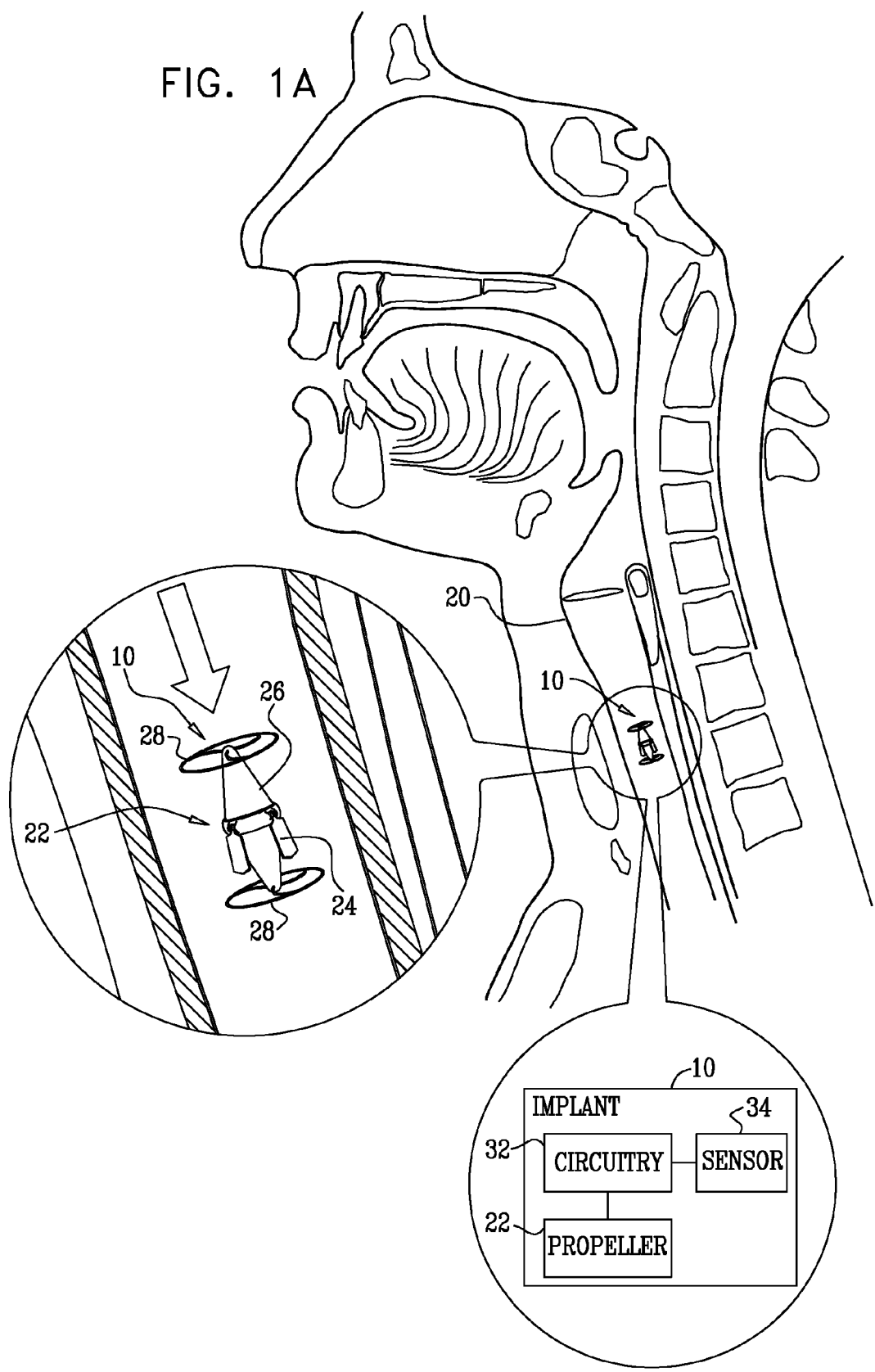
FIGS. 1A-C are schematic illustrations of a tracheal implant for providing positive pressure, in accordance with an embodiment of the present invention.
Figure 1B:
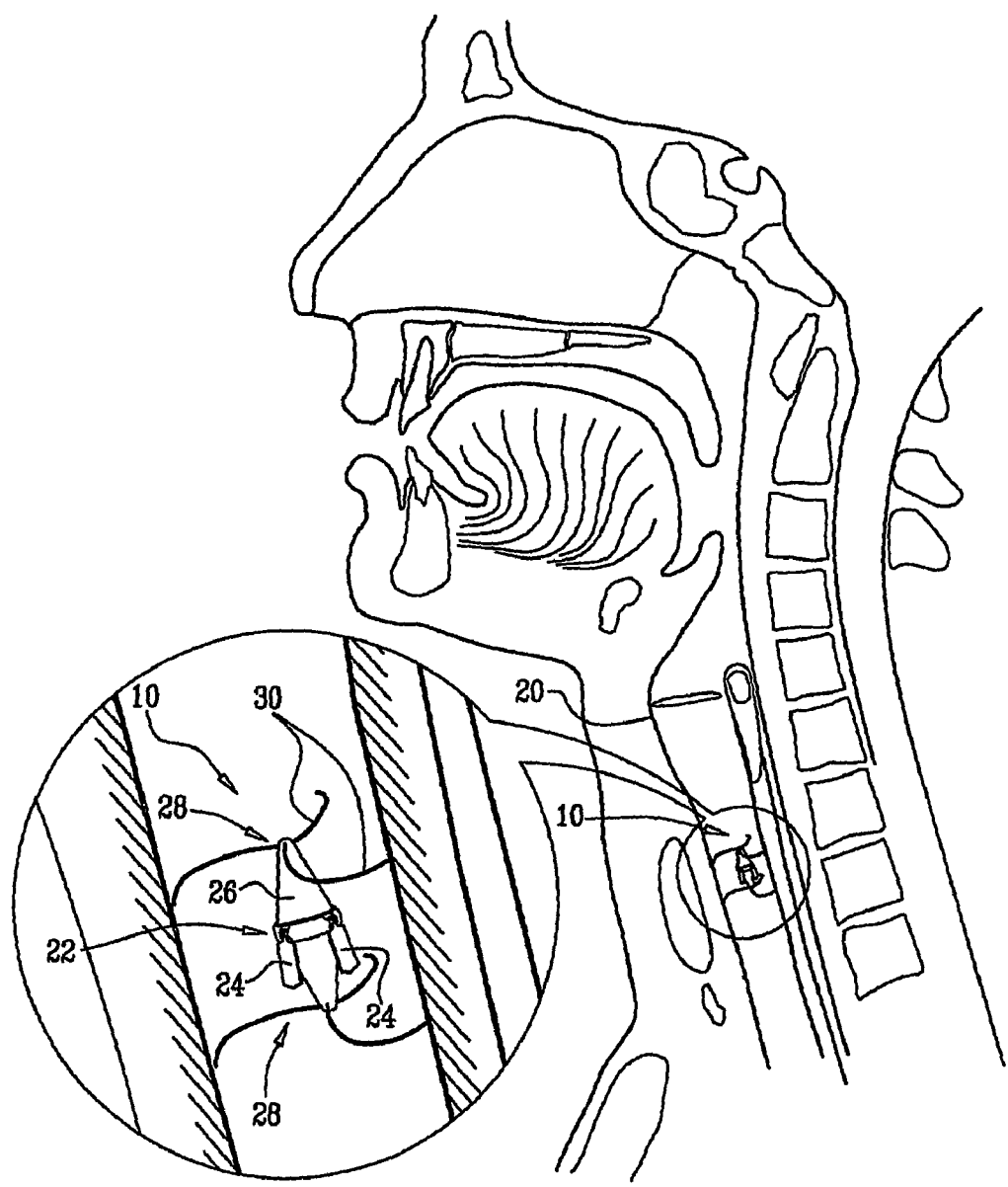
Figure 1C:
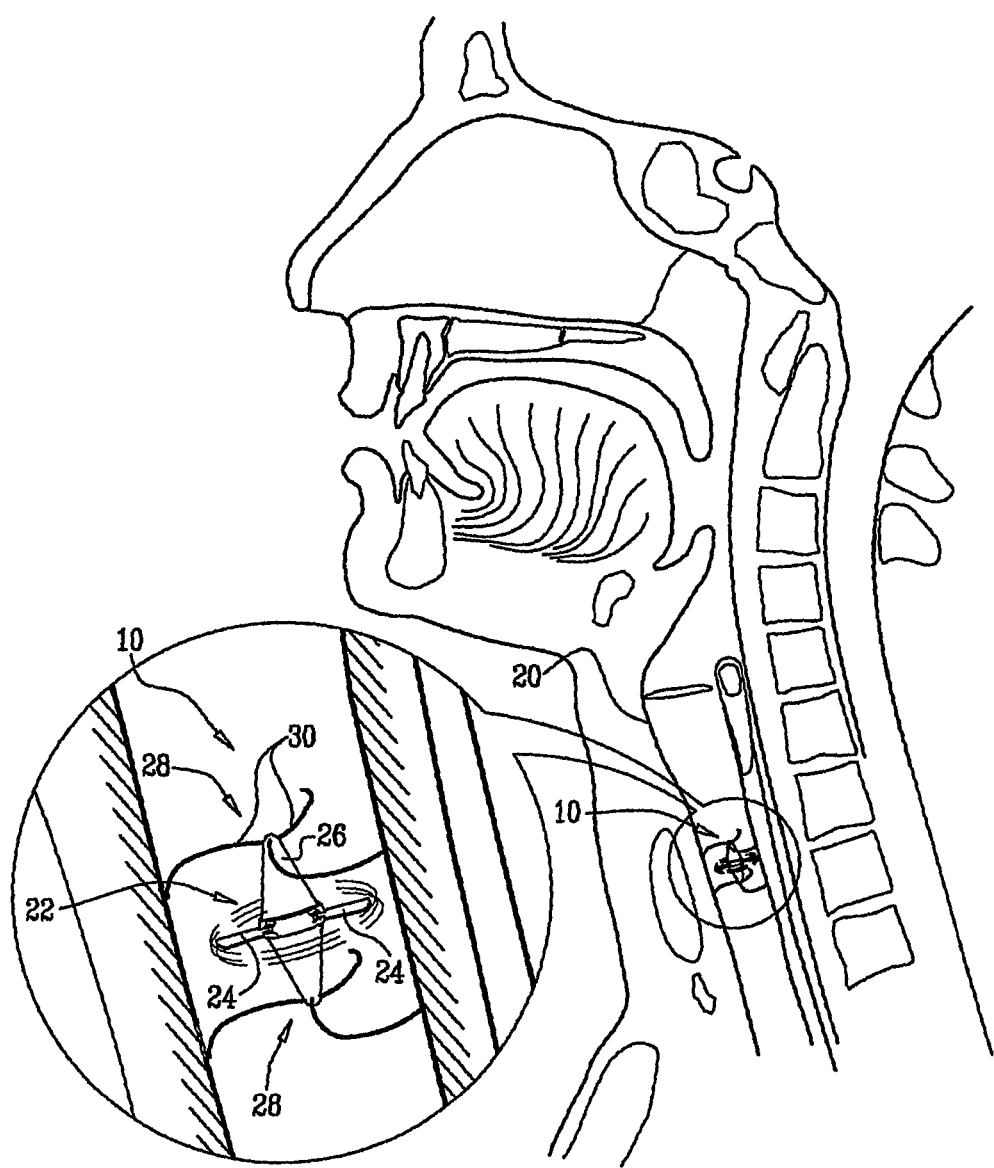

FIGS. 1A-C are schematic illustrations of a tracheal implant 10 for providing positive pressure, in accordance with an embodiment of the present invention. FIG. 1A shows implant 10 during insertion into a trachea 20 of a patient, FIG. 1B shows the implant after it has been coupled to the trachea, and FIG. 1C shows the implant during operation thereof.

Tracheal implant 10 comprises a housing 26 and at least one propeller 22 coupled thereto. The propeller comprises one or more blades 24. Housing 26 comprises an anchoring mechanism 28, which is adapted to couple implant 10 to an inner surface of trachea 20. For some applications, anchoring mechanism 28 comprises a plurality of wire springs 30, which are configured, upon expansion, to come in contact with the inner surface of the trachea. For example, the springs may be generally spiral-shaped as shown in the figures. The springs typically are appropriately configured and/or coated to reduce the likelihood of damage to the inner surface of the trachea. For some applications, the anchoring mechanism comprises a stent (not shown) sized to adhere to the inner surface of the trachea. Alternative anchoring mechanisms will be evident to those skilled in the art who have read the present application, and are within the scope of the present invention.

For some applications, housing 26 is releasably coupled to anchoring mechanism 28, in order to facilitate replacement of the propeller, a power supply, a drug reservoir, circuitry, or other portions of implant 10, while the anchoring mechanism remains coupled to the trachea, should such replacement be necessary. This replacement technique may be particular useful if fibrous tissue grows on anchoring mechanism 28. The scope of the present invention includes using such a technique to replace electrical or electromechanical apparatus implanted in other parts of the body (e.g., coupled to the heart or to an abdominal organ), while maintaining an anchoring mechanism of the apparatus in place.

As shown in FIG. 1C, after implant 10 has been coupled to trachea 20, the propeller is activated to deliver positive pressure to the trachea. For some applications, implant 10 comprises a power source, such as a rechargeable battery, while for other applications, the implant is powered wirelessly or via wires by an external power source or by a subcutaneously implanted power source. For some applications in which the implant comprises a rechargeable battery, the battery is wirelessly recharged, such as by using induction, RF energy, or ultrasound energy. Alternatively, the battery is recharged using a wire, which passes, for example, through the nose or mouth, or through the wall of the trachea. For some applications, the wire is coupled to a bite plate, which is adapted to be placed in the mouth.

Implant 10 typically comprises circuitry 32 that drives the propeller to rotate. For some applications, the circuitry is configured to drive the propeller to apply positive pressure in one or more conventional ventilation modes, such as volume ventilation, pressure-controlled ventilation, bi-level positive airway pressure (BIPAP) ventilation, inspiratory positive airway pressure (IPAP) ventilation, continuous positive airway pressure (CPAP) ventilation, or pressure-controlled ventilation (PCV), or other ventilation modes currently known in the art or developed in the future. In an embodiment, implant 10 provides a controllable level of positive end expiratory pressure (PEEP). For ventilation modes that require monitoring of respiration, such as BIPAP ventilation, implant 10 comprises a sensor 34 that detects the patient's respiration, and circuitry 32 drives the propeller responsively to at least one parameter of the respiration. For example, the sensor may comprise a pressure sensor coupled to housing 26 (e.g., above or below propeller 22), and the pressure sensor and/or the circuitry may be configured to detect pressure fluctuations between about 0.05 and 1 Hz.

For some applications, the circuitry regulates the pressure applied by the propeller by setting the rate of rotation of the propeller, and/or by setting an angle of inclination of the blades.

For some applications, implant 10 comprises a cylindrical tube (e.g., a tracheal stent) that surrounds housing 26 and blades 24, to reduce the likelihood that the blades may come in contact with the wall of the trachea during operation of the implant. Alternatively, the housing is shaped so as to define an inlet and outlet that together define a flow path, and the blades are positioned within the housing in the flow path.

In an embodiment, implant 10 comprises an activity sensor, e.g., an accelerometer, or a respiration rate or heart rate monitor, and increases the propeller speed or otherwise modulates the operation of the implant in response to an increase in the patient's level of activity. Alternatively or additionally, implant 10 operates in accordance with a schedule, and/or reduces its level of operation when the patient is sleeping. For example, the implant may comprise a clock for determining when the patient is generally sleeping, or another physiological sensor that generates a signal indicative of sleeping by the patient.

In an embodiment of the present invention, a drug-release tracheal implant comprises a drug reservoir for holding a drug, and an application mechanism. that releases the drug from the reservoir into the trachea. For example, the mechanism may be adapted to spray the drug into the trachea. For some applications, the implant comprises circuitry adapted to actuate the application mechanism. For example, the circuitry may be configured to regulate a dosage or timing of administration of the drug. For some applications, the circuitry is adapted to receive a signal, either wirelessly or over wires, and to regulate the administration of the drug responsively to the signal. For example, the signal may be an acoustic signal indicative of the onset of a transient pathological respiratory condition, or a pressure signal indicative of the onset of a transient pathological respiratory condition. For some applications, implant 10 comprises the drug reservoir and the application mechanism.

"Propeller," as used in the present application, including in the claims, is to be understood as including any mechanical device that rotates to push air, including fans and turbines.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an implant, which comprises:
   a housing configured to be implanted in a trachea of a patient;
   a propeller, coupled to the housing, and configured to generate a positive pressure in the trachea; and
   circuitry, configured to drive the propeller to apply the positive pressure using a ventilation mode selected from the group consisting of inspiratory positive airway pressure, and continuous positive airway pressure, while the propeller is in the trachea.

2. The apparatus according to claim 1, wherein the circuitry is configured to regulate the positive pressure generated by the propeller by setting a rate of rotation of the propeller.

3. The apparatus according to claim 1, wherein the propeller comprises one or more blades, wherein the housing is shaped so as to define an inlet and outlet that together define a flow path, and wherein the blades are positioned within the housing in the flow path.

4. The apparatus according to claim 1, wherein the apparatus is configured to treat a condition of the patient selected from the group consisting of: congestive heart failure, a pulmonary condition, pulmonary edema, chronic obstructive pulmonary disease (COPD), sleep apnea, obstructive sleep apnea, and emphysema.

5. The apparatus according to claim 1, wherein the circuitry is configured to drive the propeller to generate the positive pressure in accordance with a schedule.

6. The apparatus according to claim 1, wherein the circuitry is configured to drive the propeller to reduce a level of operation when the patient is sleeping.

7. The apparatus according to claim 1, wherein the housing comprises an anchoring mechanism, which is configured to couple the housing to an inner surface of the trachea.

8. The apparatus according to claim 7, wherein the anchoring mechanism comprises a plurality of wire springs, which are configured, upon expansion, to come in contact with the inner surface of the trachea.

9. The apparatus according to claim 8, wherein the springs are generally spiral-shaped.

10. The apparatus according to claim 1, wherein the propeller is configured to generate the positive pressure at a low level that provides a constant state of expansion of alveoli of the patient.

11. The apparatus according to claim 10, wherein the apparatus is configured to treat emphysema of the patient.

12. The apparatus according to claim 1, further comprising a sensor configured to sense at least one parameter of respiration of the patient, wherein the circuitry is configured to drive the propeller responsively to the at least one parameter.

13. The apparatus according to claim 12, wherein the sensor comprises a pressure sensor.

14. The apparatus according to claim 13, wherein the pressure sensor is configured to detect pressure fluctuations between 0.05 and 1 Hz.

15. The apparatus according to claim 13, wherein the circuitry is configured to detect pressure fluctuations between 0.05 and 1 Hz.

16. The apparatus according to claim 1, further comprising an activity sensor, which is configured to sense a level of activity of the patient, wherein the circuitry is configured to modulate a parameter of operation of the propeller responsively to the sensed level of activity of the patient.

17. The apparatus according to claim 16, wherein the activity sensor is selected from the group consisting of: an accelerometer, and a heart rate monitor.

18. The apparatus according to claim 16, wherein the circuitry is configured to increase a speed of the propeller in response to an increase in the sensed level of activity.

19. The apparatus according to claim 1, wherein the selected ventilation mode is inspiratory positive airway pressure, and wherein the circuitry is configured to drive the propeller to apply the positive pressure using the inspiratory positive airway pressure mode of ventilation.

20. The apparatus according to claim 1, wherein the selected ventilation mode is continuous positive airway pressure, and wherein the circuitry is configured to drive the propeller to apply the positive pressure using the continuous positive airway mode of ventilation.

21. Apparatus comprising an implant, which comprises:
a housing configured to be implanted in a trachea of a patient;
a propeller, coupled to the housing, and configured to generate a positive pressure in the trachea; and
circuitry configured to drive the propeller to generate a controllable level of positive end expiratory pressure (PEEP), while the propeller is in the trachea.

22. A method comprising:
implanting a propeller in a trachea of a patient; and
activating the propeller to generate a positive pressure in the trachea, using a ventilation mode selected from the group consisting of inspiratory positive airway pressure, and continuous positive airway pressure.

23. The method according to claim 22, wherein activating the propeller comprises regulating the positive pressure generated by the propeller by setting a rate of rotation of the propeller.

24. The method according to claim 22, wherein implanting the propeller comprises selecting the patient for implantation of the propeller because the patient suffers from a condition selected from the group consisting of: congestive heart failure, a pulmonary condition, pulmonary edema, chronic obstructive pulmonary disease (COPD), sleep apnea, obstructive sleep apnea, and emphysema.

25. The method according to claim 22, wherein activating the propeller comprises activating the propeller to generate the positive pressure in accordance with a schedule.

26. The method according to claim 22, wherein activating the propeller comprises configuring the propeller to reduce a level of rotating of the propeller when the patient is sleeping.

27. The method according to claim 22, comprising providing supplemental oxygen in conjunction with activating the propeller.

28. The method according to claim 22, wherein activating the propeller comprises activating the propeller to generate the positive pressure at a low level that provides a constant state of expansion of alveoli of the patient.

29. The method according to claim 28, wherein implanting the propeller comprises selecting the patient for implantation of the propeller because the patient suffers from emphysema.

30. The method according to claim 22, wherein generating the positive pressure comprises sensing at least one parameter of respiration of the patient, and rotating the propeller responsively to the at least one parameter.

31. The method according to claim 30, wherein sensing the at least one parameter comprises sensing a pressure.

32. The method according to claim 31, wherein sensing the pressure comprises detecting pressure fluctuations between 0.05 and 1 Hz.

33. The method according to claim 22, wherein generating the positive pressure comprises sensing a level of activity of the patient using an activity sensor, and modulating a parameter of operation of the propeller responsively to the sensed level of activity of the patient.

34. The method according to claim 33, wherein sensing the activity comprises sensing activity of the patient selected from the group consisting of: motion of the patient, and a heart rate of the patient.

35. The method according to claim 33, wherein generating the positive pressure comprises increasing a rate of rotation of the propeller in response to an increase in the sensed level of activity.

36. The method according to claim 22, wherein the selected ventilation mode is inspiratory positive airway pressure, and wherein activating the propeller comprises activating the propeller to generating the positive pressure using the inspiratory positive airway pressure mode of ventilation.

37. The method according to claim 36, wherein generating the positive pressure comprises sensing a level of activity of the patient using an activity sensor, and increasing a rate of rotation of the propeller in response to an increase in the sensed level of activity.

38. The method according to claim 22, wherein the selected ventilation mode is continuous positive airway pressure, and wherein activating the propeller comprises activating the propeller to generating the positive pressure using the continuous positive airway mode of ventilation.

39. A method comprising:
implanting a propeller in a trachea of a patient; and
activating the propeller to generate a controllable level of positive end expiratory pressure (PEEP).

40. Apparatus comprising an implant, which comprises:
a housing configured to be implanted in a trachea of a patient;
a propeller, coupled to the housing, and configured to generate a positive pressure in the trachea; and
circuitry, configured to drive the propeller to apply the positive pressure using a bi-level positive airway pressure mode of ventilation, while the propeller is in the trachea.

41. The apparatus according to claim 40, further comprises an activity sensor, which is configured to sense a level of activity of the patient, wherein the circuitry is configured to increase a speed of the propeller in response to an increase in the sensed level of activity.

42. A method comprising:
implanting a propeller in a trachea of a patient; and
activating the propeller to generate a positive pressure in the trachea, using a bi-level positive airway pressure mode of ventilation.

* * * * *